United States Patent [19]

Payne et al.

[11] 4,405,171

[45] Sep. 20, 1983

[54] OVERHEAD AMBULANCE ATTENDANT STABILIZING DEVICE

[76] Inventors: Arnold F. Payne, W. 1724 York, Spokane, Wash. 99205; Gene A. Mauro, E. 14016 Mallon, Spokane, Wash. 99216; Wayne L. Cumpton, 4923 Powell Rd., Newman Lake, Wash. 99025; George J. Orr, 13422 E. 6th, Spokane, Wash. 99216

[21] Appl. No.: 334,525

[22] Filed: Dec. 28, 1981

[51] Int. Cl.[3] .......................... B60P 3/26; A61B 19/00

[52] U.S. Cl. ...................................... 296/19; 128/1 R

[58] Field of Search ................ 128/133; 272/117, 125, 272/144, 70, 70.3, 70.4, 116, 134, 136; 273/55 R, 55 A; 280/751; 296/19

[56] References Cited

U.S. PATENT DOCUMENTS 2,696,383 12/1954 Noftsinger ........................ 273/55 R 3,304,089 2/1967 Smith ................................ 273/55 R 4,241,913 12/1980 Zwayer et al. ...................... 272/134

*Primary Examiner*—Kyle L. Howell

*Assistant Examiner*—Karin M. Reichle

*Attorney, Agent, or Firm*—Wells, St. John & Roberts

[57] ABSTRACT

A stabilizing device is described for bracing an ambulance attendant in proper position for administering cardiopulmonary resuscitation (CPR) while the ambulance is in transit. The device is roof mounted and includes two pivoted arms that may be selectively moved from horizontal storage positions, adjacent the ambulance roof to substantially vertical downward operative positions. Shoulder pads are slidably mounted to the arms. The attendant may lean against the pads to secure himself in proper position for administration of CPR. The pads are slidable on the arms to allow free vertical motion of the attendant's shoulders and to automatically adjust for shoulder height.

12 Claims, 5 Drawing Figures

FIG 4
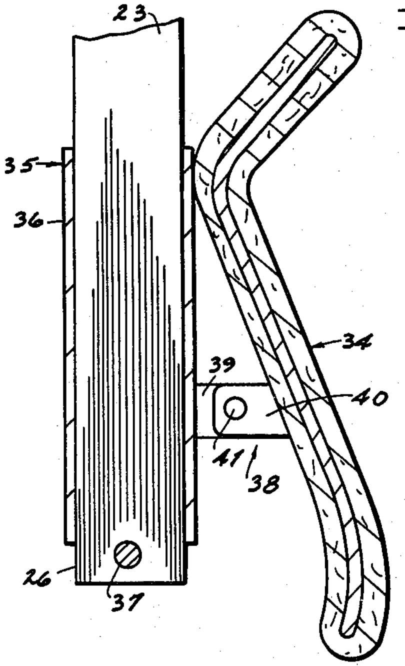
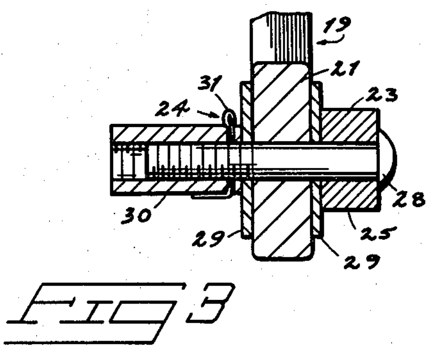
FIG 3
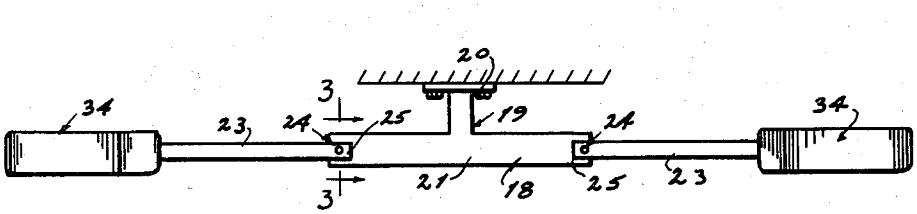
FIG 5

OVERHEAD AMBULANCE ATTENDANT STABILIZING DEVICE

BACKGROUND OF THE INVENTION

The present invention is related to devices for stabilizing an ambulance attendant in relation to a patient lying on the ambulance bed during transit, to facilitate administration of cardiopulmonary resuscitation.

A percentage of ambulance calls are made for victims of heart dysfunction or other trauma that affects proper functioning of the heart. It is not unusual that cardiac arrest occurs before the patient can be moved to a hospital facility. Cardiopulmonary resuscitation (CPR) must than be administered immediately while the patient is moved to the proper care facility.

Proper administration of CPR rquires substantially vertical downward rhythmic depressions of the chest cavity immediately over the heart. The rhythm, force, and angle of thrust are very important to maintain circulation and stimulate the heart muscle. It is very important that CPR not be interrupted or that its rhythm be changed. Such disruptions can have serious, even fatal, consequences for the patient.

Much difficulty has been experienced in administering CPR in a moving ambulance. The attendant often must brace himself with one arm while trying to administer CPR with a free hand. This situation is far from ideal, especially since CPR is properly administered using both hands. Further, when the vehicle encounters rough terrain or must brake or make a turn, administration even with only one hand becomes difficult or impossible. There is also the safety of the attendant to be considered. Administration of CPR to a patient on an ambulance bed requires that the attendant stand over the patient. Sudden vehicle movement can throw the attendant off balance and possibly result in serious injury to the attendant.

There is therefore a serious need for the attendant to maintain a secure position in relation to the patient so CPR can be properly maintained and so the attendant will feel his own safety is secure. This must be done without interfering with access to the patient. The area must be clear to allow performance of other needed functions.

BRIEF DESCRIPTION OF THE DRAWINGS

A preferred embodiment of the present invention is shown in the accompanying drawings in which:

FIG. 3 is an enlarged sectional view taken along line 3—3 in FIG. 5;

FIG. 4 is an enlarged sectional view taken along line 4—4 in FIG. 2; and

FIG. 5 is a side elevation view showing the present device in an elevated horizontal storage position.

DETAILED DESCRIPTION OF A PREFERRED EMBODIMENT

The following disclosure is submitted in compliance with the constitutional purpose of the patent laws to "promote the progress of science and the useful arts".

Figure 1:
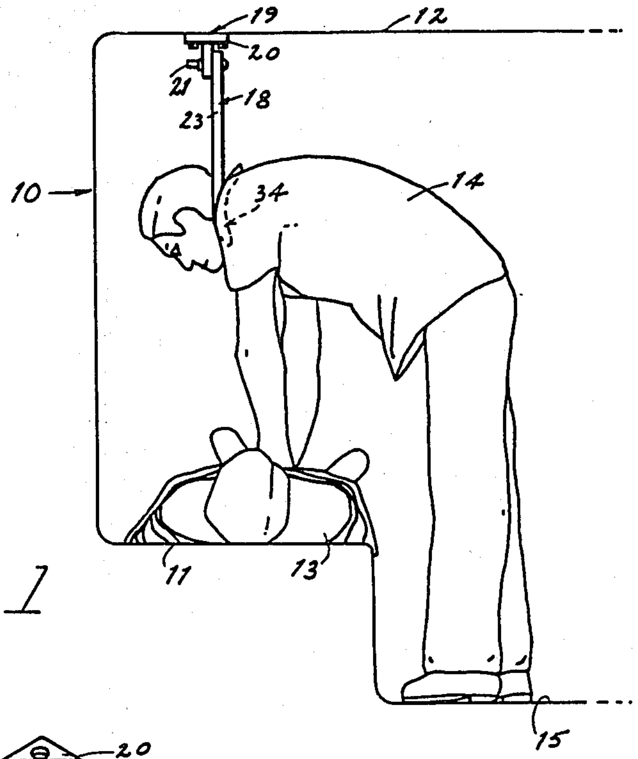
FIG. 1 is a pictorial view of the present invention, showing its function and with a portion of an ambulance being shown diagrammatically.

To facilitate a better understanding of the invention, FIG. 1 shows diagrammatically a section through an ambulance generally designated by the numeral 10. The ambulance 10 includes an ambulance bed 11 that extends longitudinally with respect to the length of the vehicle. Often, ambulances have two or more such beds. The ambulance roof is diagrammatically illustrated at 12.

A patient 13 is illustrated lying on the ambulance 11 and an attendant 14 is shown in position over the patient administering cardiopulmonary resuscitation (CPR). It is noted the attendant 14 is standing on the ambulance floor 15 and bending over the patient 13 to properly position his shoulders and arms directly over the chest cavity of the patient. It is the purpose of the present invention to selectively stabilize the attendant in this position so that CPR may be properly administered while the ambulance is in transit without endangering either the patient or attendant.

The present stabilizing device is generally designated at 18. The device is mounted to the ambulance roof 12 to secure and position the attendant's shoulders vertically over the patient's thorax, thereby facilitating application of CPR. The device is selectively operable to be shifted between the operative position illustrated in FIG. 1 and 2 and an inoperative position as illustrated in FIG. 5.

The present stabilizing device 18 includes a mounting bracket 19 that is adapted to be secured to the ambulance roof 12. The bracket 19 may be attached by bolts or other appropriate rigid fastening mechanisms to the ambulance roof through provision of a mounting plate 20. A horizontal rigid bar 21 is affixed to the mounting plate 20 and preferably extends longitudinally with respect to the ambulance bed when the bracket is properly mounted to the ambulance roof.

Figure 2:
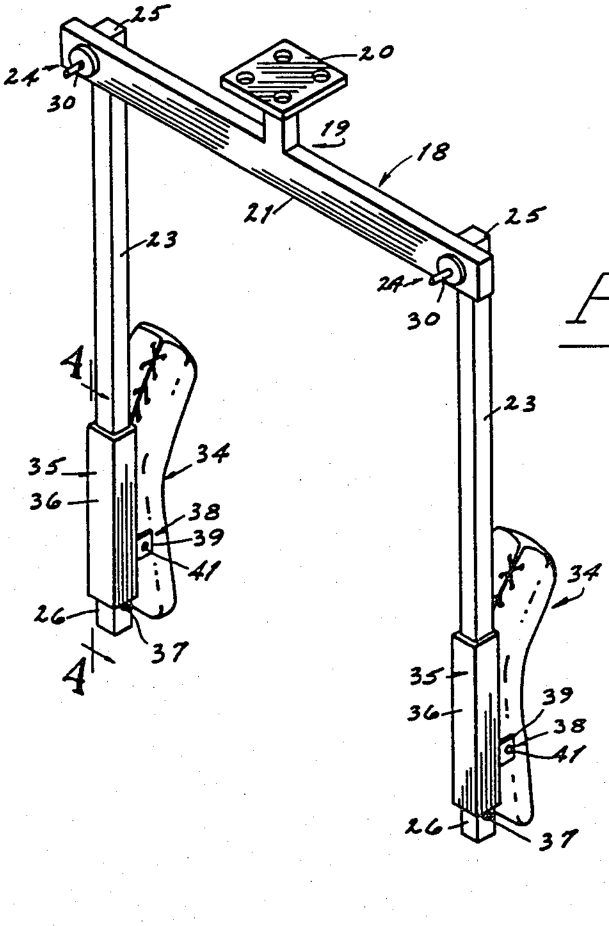
FIG. 2 is a pictorial view of the present stabilizing device.

Shoulder arms 23 are pivotably mounted to opposite ends of the rigid bar 21. The shoulder arms 23 are mounted by means 24 for securing the two shoulder arms in the inoperative storage position shown in FIG. 5 and in depending operative positions as shown in FIGS. 1 and 2. The shoulder arms include upper ends 25 that are pivotally mounted to the rigid bar 21 and free lower ends 26. Preferably the shoulder arms arm of equal length and formed of a rigid material.

Means 24 may be comprised of clamp bolts 28 that extend through the shoulder arms 23 and the rigid bar 21 (FIG. 3). Friction disks 29 are sandwiched between the shoulder arms 23 and rigid bar 21 and secured by nuts 30. Cotter pins 31 may be utilized to lock the nuts 30 in position. The friction disks 29 and the clamping force produced through the bolts 28 and nuts 30 produce a selected resistance to pivotal motion of the shoulder arms between the operative and inoperative positions. It is preferred that the shoulder arms "give" longitudinally to avoid injury to the attendant should the ambulance itself be involved in an accident. However, it is important that the shoulder arms resist other than abnormal longitudinal forces in order to secure the attendant in proper position while the ambulance is in transit.

Shoulder pads 34 are operatively mounted to the two shoulder arms for engaging the attendant's shoulders while he administers CPR to the patient 13. The shoulder pads 34 provide a comfortable brace or rest against which the attendant may lean and which, along with the arms 23, will minimize fore and aft movement of the attendant while the ambulance is in transit. Specifically, the shoulder pads are concave and face the attendant to receive areas of the upper pectorals, clavicle, and trapezius. The pads thus engage a large enough area to avoid discomfort or injury to the attendant. The pads are covered with a soft resilient material to further enhance comfort and safety.

The shoulder pads 34 are preferably mounted by slide means 35 on the shoulder arms 23. The slide means 35 allow the shoulder pads to slide freely along the lengths of the shoulder arms, thereby automatically adjusting for the attendant's height and allowing for vertical motion of the attendant's shoulders.

The slide means 35 may include channel members 36 slidably mounted over the arms 23.

The shoulder pads 34 are preferably mounted by slide means 35 on the shoulder arms 23. The slide means allow the shoulder pads to slide freely along the lengths of the shoulder arms, thereby automatically adjusting for the height and allowing for vertical motion of the attendant's shoulders.

The slide means 35 may include channel members 36 slidably mounted over the arms 23. The channels 36 will slide freely over the lengths of the arms between the upper ends 25 and abutments 37 at the lower ends 26. The abutments 37 may simply be comprised of pins or bolts mounted to the shoulder arms in the slide paths of the channels 36. The abutments 37 will therefore prevent the shoulder pads from sliding downwardly off the ends of the shoulder arms.

It is preferred that the shoulder pads 34 be mounted by a pivot means 38 for pivotal motion about horizontal axes when the shoulder arms are in their depending operating positions. The pivot means 38 may mount the shoulder pads to the slide means 35. Means 38 may be comprised of interfitting brackets 39 and 40 on the slide channels 36 and shoulder pads 34 respectively. Pivot pins 41 extend through the respective brackets to define the horizontal pivot axis for each pad.

The present stabilizing device may be mounted to existing ambulance roofs simply by drilling appropriate holes and securing appropriate mounting bolts through the mounting plate 20 and adjacent roof structure. Care should be taken in properly positioning the bracket in relation to the ambulance bed 11. The device should be mounted over the bed so the shoulder pads 34, when in the downward operative positions, will brace an attendant's shoulders and upper torso directly over the chest of a paitent lying on the ambulance bed.

It is also important that the device be mounted so the horizontal bar 21 extends substantially longitudinally with respect to the ambulance bed. This orients the pivot axes for the shoulder arms substantially transversely and horizontal. The arms will therefore fold between an inoperative position as shown in FIG. 5 wherein the arms extend longitudinally above the ambulance bed. In this position, the arms are out of the way for the various operations during transport of patients not requiring CPR or other aid that would require the steady positioning of an attendant. The securing means 24 assures that the arms and shoulder pads will remain in the horizontal, inoperative positions unitl forced downwardly to the lowered, operative positions. It is possible that the rigid bar 21 and arms 23 can be used in the inoperative positions, to support other equipment. For example, intraveneous bags can be suspended from the arms or plate.

When it becomes necessary to administer CPR or when the attendant otherwise wishes to remain in a secure position over a patient lying on the ambulance bed, the shoulder arms may be forceably pivoted downward to their operative positions. This is done simply by pulling downwardly on the outward or downward arm ends 26, causing the arms to be pivoted to substantially vertical, depending operative positions. When this is done, the attendant may position himself with his shoulder area, specifically the upper pectorals, clevicles, and trapezius in the complementary concave surfaces of the shoulder pads. He may lean against the pads and arms to brace himself in the desired position. The slide means 35 will allow up and downward motion of the attendant as the channels 36 slide freely along the shoulder arms. This allows for free vertical movement of the upper torso of the attendant while maintaining the desired stabilizing function.

CPR can be performed using the above described stabilizing device in a proper and continuous manner over nearly any roadway conditions. Actual use of the device indicates substantially improved conditions for administration of CPR during transit and it may be assumed that a higher survival rate of severe trauma patients during transit is made possible with the present device. The slide means 35 provides the distinct advantage of allowing free vertical motion of the attendant's shoulders while the arms maintain the shoulders in proper position with respect to the patient. This allows normal "floating" position of the attendant's shoulders during administration of CPR, without the stabilizing device adversely affecting the rhythmic application of thrust produced through the attendant's arms. Furthermore, the sliding shoulder pads automatically adjust to the height and arm length of the attendant. This is a substantial advantage where immediate action is essential.

The longitudinal orientation of the arms over the patient and ambulance bed has additional advantages among those listed above. The horizontal and longitudinally oriented arms are completely clear of the patient. This is true both when the arms are in the inoperative horizontal positions and the downwardly depending operative positions. The area around the patient remains clear for administering by other attendants or to facilitate application of other aids, such a intraveneous tubes, traction devices, etc. Furthermore, the bracket 19 and arms 23 are clear of the normal head room for the attendants and do not present significant danger of injury to the attendant.

The horizontal transverse pivot axes for the shoulder arms 23, coupled with the securing means 24 allow selective pivotal motion of the arms between the operative and inoperative positions. It is important that the axes be transverse for the safety of the operator and for proper location of the shoulder arms within the ambulance structure. For example, if the ambulance were to be involved in a collision either from the front or back during transit, an attendant administering CPR and using the stabilizing device would be thrown forward or rearward against one or the other of the arms. The soft shoulder pad and supporting arm will resist and partially restrain movement of the attendant during impact. However, the restraint is not rigid and the affected arm will pivot upwardly out of the path of the attendant. This is important since rigid bracing of the shoulder arms and pads could otherwise cause serious neck or head injury to the attendant during an accident. With the present arrangement, selected resistance is offered to abosrb a portion of the kinetic energy of the attendant while the arm and shoulder pad move clear of the attendant to avoid injury.

This description of a preferred embodiment of the invention has been presented for purposes of illustration and example. It is not intended to be exhaustive or to limit the invention to the precise form disclosed. It is intended that the scope of the invention be defined by the following claims:

We claim:

1. An overhead ambulance attendant stabilizing device for restraining a medical attendant within an ambulance having an overhead roof structure while the attendant is administering cardiopulmonary resuscitation to a patient lying on an ambulance bed while the ambulance is in transit, comprising:

bracket means for mounting the device to the overhead roof of the ambulance overlying the ambulance bed;

two elongated shoulder arms pivotally connected to the bracket means for movement between elevated outstretched horizontal storage positions adjacent the ambulance roof and depending operating positions projecting downward from the bracket toward the ambulance bed;

means for securing the two shoulder arms in the storage positions and in the depending operating positions;

shoulder pad means operatively mounted to the two shoulder arms for engaging the medical attendant's shoulders to restrain movement of the attendant with respect to the ambulance bed while the attendant is administering cardiopulmonary resuscitation to the patient on the ambulance bed.

2. The overhead ambulance attendant stabilizing device as claimed by claim 1 further comprising:

slide means mounting the shoulder pads for free sliding motion along the lengths of the shoulder arms.

3. The overhead ambulance attendant stabilizing device as claimed by claim 2 further comprising pivot means on the shoulder pads and slide means for allowing free pivotal motion of the shoulder pads about horizontal axes when the shoulder arms are in their depending operating positions.

4. The overhead ambulance attendant stabilizing device as claimed in claim 1 further comprising pivot means operatively mounting the shoulder pads to the shoulder arms for enabling the shoulder pads to pivot relative to the shoulder arm.

5. The overhead ambulance attendant stabilizing device as claimed in claim 1 wherein the means for securing the shoulder arms in the storage and operating positions is comprised of:

clamp bolts extending through the shoulder arms and bracket means; and friction discs sandwiched between the shoulder arms and bracket means.

6. The overhead ambulance attendant stabilizing device as claimed by claim 1 wherein the bracket means operatively connects the device to the overhead roof with the elongated shoulder arms extending fore and aft with respect to a longitudinal dimension of the ambulance when the shoulder arms are pivotally mounted to the bracket means for pivotal movement about transverse parallel axes to enable the shoulder arms to pivot downward and toward each to the operating positions.

7. The ambulance attendant stabilizing device as claimed by claim 1 wherein the shoulder pads are concave to conform to the upper pectorals, trapezius, and clavicle of the attendant.

8. The overhead ambulance attendant stabilizing device as claimed by claim 1 wherein the shoulder arms are of sufficient length to enable the shoulder pads to engage the attendant's shoulders when the shoulder arms are in the depending operating positions to restrain movement of the attendant with respect to the ambulance bed without interfering with the attendant's administration of cardiopulmonary resuscitation.

9. The overhead ambulance attendant stabilizing device as claimed by claim 8 wherein the bracket means operatively connects the device to the overhead roof with the elongated shoulder arms extending fore and aft with respect to a longitudinal dimension of the ambulance when the shoulder arms are in the storage positions and wherein the shoulder arms are pivotally mounted to the bracket means for pivotal movement about transverse parallel axes to enable the shoulder arms to pivot downward and inward toward each other to the operating positions.

10. The overhead ambulance attendant stabilizing device as claimed by claim 9 further comprising:

slide means mounting the shoulder pads for free sliding motion along the lengths of the shoulder arms.

11. The overhead ambulance attendant stabilizing device as claimed by claim 10 wherein the means for securing the shoulder arms in the storage and operating positions is comprised of:

clamp bolts extending through the shoulder arms and bracket means; and friction discs sandwiched between the shoulder arms and bracket means.

12. The overhead ambulance attendant stabilizing device as claimed by claim 11 further comprising pivot means on the shoulder pads and slide means for allowing free pivotal motion of the shoulder pads and transverse pivot axes.

* * * * *